(12) United States Patent
Jones

(10) Patent No.: US 8,834,566 B1
(45) Date of Patent: Sep. 16, 2014

(54) PRESBYOPIA-CORRECTING INTRAOCULAR LENS IMPLANT

(76) Inventor: David Jones, Davie, FL (US)

(*) Notice: Subject to any disclaimer, the term of this patent is extended or adjusted under 35 U.S.C. 154(b) by 0 days.

(21) Appl. No.: 13/611,526

(22) Filed: Sep. 12, 2012

(51) Int. Cl.
*A61F 2/16* (2006.01)

(52) U.S. Cl.
USPC .................. 623/6.22; 623/6.37; 623/6.34

(58) Field of Classification Search
USPC ............ 623/6.37, 4.1, 6.13, 6.22, 6.32, 6.34, 623/6.38
See application file for complete search history.

(56) References Cited

U.S. PATENT DOCUMENTS

| | | | |
|---|---|---|---|
| 4,787,903 A | 11/1988 | Grendahl | |
| 4,816,031 A | 3/1989 | Pfoff | |
| 5,108,429 A * | 4/1992 | Wiley | 623/6.22 |
| 5,712,721 A | 1/1998 | Large | |
| 5,800,530 A | 9/1998 | Rizzo, III | |
| 5,800,533 A | 9/1998 | Eggleston et al. | |
| 6,120,538 A | 9/2000 | Rizzo, III et al. | |
| 6,638,304 B2 * | 10/2003 | Azar | 623/6.22 |
| 6,645,245 B1 * | 11/2003 | Preussner | 623/6.22 |
| 6,796,942 B1 | 9/2004 | Kreiner et al. | |
| 6,908,196 B2 | 6/2005 | Herekar et al. | |
| 7,001,427 B2 | 2/2006 | Aharoni et al. | |
| 7,238,201 B2 | 7/2007 | Portney et al. | |
| 7,964,833 B2 | 6/2011 | Holladay | |
| 2004/0148022 A1 | 7/2004 | Eggleston | |
| 2005/0119740 A1 | 6/2005 | Esch et al. | |
| 2005/0209691 A1 * | 9/2005 | Aharoni et al. | 623/6.11 |
| 2005/0256571 A1 * | 11/2005 | Azar | 623/6.22 |
| 2006/0095128 A1 | 5/2006 | Blum et al. | |
| 2006/0122531 A1 * | 6/2006 | Goodall et al. | 600/546 |
| 2007/0088433 A1 | 4/2007 | Esch et al. | |
| 2007/0100443 A1 * | 5/2007 | Peyman | 623/6.13 |
| 2007/0100445 A1 | 5/2007 | Shadduck | |
| 2008/0021549 A1 * | 1/2008 | Eagan et al. | 623/6.22 |
| 2010/0004741 A1 * | 1/2010 | Gupta et al. | 623/6.22 |
| 2013/0245754 A1 * | 9/2013 | Blum et al. | 623/6.13 |

OTHER PUBLICATIONS

Britannica Online definition of "silicone" (2013).*

* cited by examiner

*Primary Examiner* — Paul Prebilic
(74) *Attorney, Agent, or Firm* — Gold & Rizvi, P.A.; Glenn E. Gold

(57) ABSTRACT

A presbyopia correcting intraocular lens implant for implanting in a human eye includes an implant body having a central lens enclosure and at least one stability tab extending therefrom. At least one ciliary body sensor senses movement of the eye's ciliary body. An electronic module is embedded in the implant body and includes a microprocessor communicative with the ciliary body sensor. A dynamic lens assembly is housed in the central lens enclosure and has a dynamic range of continuous accommodation. The lens implant also includes a renewable intraocular power supply.

18 Claims, 7 Drawing Sheets

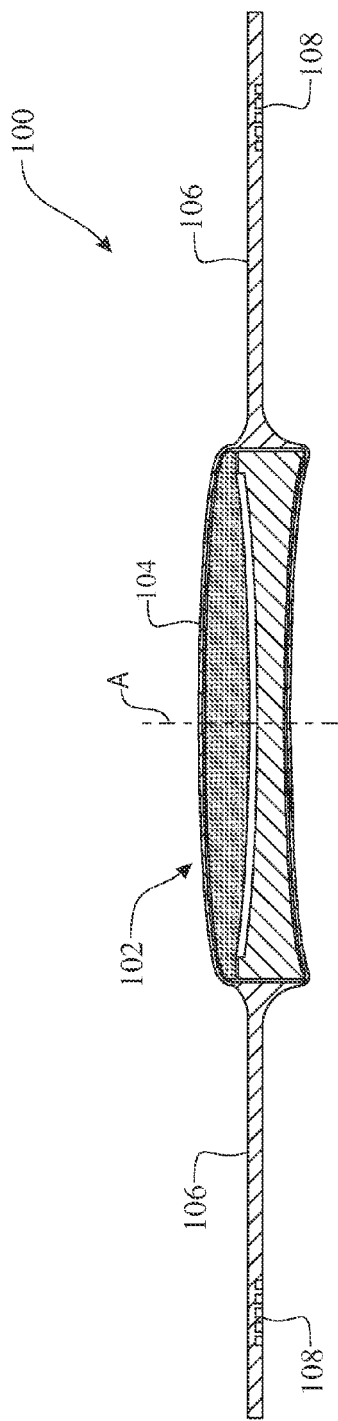
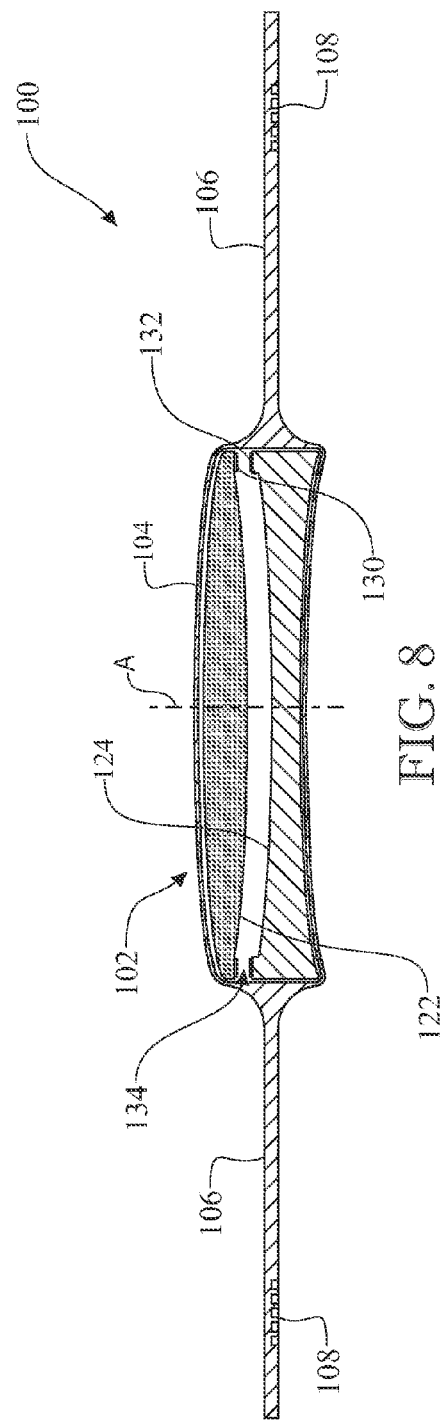

PRESBYOPIA-CORRECTING INTRAOCULAR LENS IMPLANT

FIELD OF THE INVENTION

The present disclosure generally relates to an implantable intraocular lens, and more particularly to an implantable intraocular lens for the correction of presbyopia that is responsive to movement of the eye's ciliary body.

BACKGROUND OF THE INVENTION

Aging is a physiological process of physical changes over time and is encountered by all living organisms. The human body is not immune to this process and is manifested in many forms. Just as hair begins to turn gray and skin begins to wrinkle, one sign of aging in the human body is the degradation of eye functions. In particular, all humans living beyond the age of their mid-40's begin to experience the effects of presbyopia. Presbyopia is the condition wherein the human eye exhibits a progressively diminished ability to focus on near objects and is most commonly experienced when reading.

The exact mechanisms of presbyopia are not known with certainty, however research evidence most strongly supports a loss of elasticity of the crystalline lens. The periphery of the crystalline lens is attached via the zonular apparatus of Zinn to the ciliary body which comprises the ciliary processes and the ciliary muscle and is located in the anterior portion of the human eye. One function of the ciliary body is to produce and regulate the flow of aqueous humor with respect to the anterior chamber of the eye. Another function of the ciliary body involves its musculature. The ciliary muscle is a ring of smooth muscle comprising longitudinal and circular fibers within the ciliary body in the eye's middle layer that, among its other functions, controls accommodation or changing of the shape of the lens within the eye for transitioning the focus of the eye between near objects and far objects. This dynamic mechanism of natural accommodation manifests in real time via a neural feedback loop involving the central and autonomic nervous systems wherein image quality on the retina drives ciliary muscle tone effecting the crystalline lens position and shape to achieve image clarity at varying object distances. The loss of accommodation continues such that by a person's 50's, intermediate vision is affected making it more difficult to work on a computer or read sheet music. By the time a person reaches 70 years of age, there is minimal to no accommodative capacity remaining in the eyes.

In a normally functioning eye, the cornea and crystalline lens of the eye work in concert to focus a clear image on the retina. The cornea provides the bulk of the focusing power and the lens provides the fine-tune focusing. The natural crystalline lens in the eye is flexible and according to the Hemholtz theory of accommodation the lens changes shape and becomes more globular upon ciliary muscle contraction allowing the focusing system of the eye to accommodate, or increase its dioptric power, providing focus at near distances. The degree of accommodation in humans declines with age such that at around 8 years of age, the range of accommodation is about 14 diopters. By the time a person reaches 40 years, the range has decreased to 6 diopters, and when a person reaches 68 years the range is further reduced to 0.5 diopters. Measurements in non-human primates indicate that the ciliary body still functions in mature adults and that presbyopia is ostensibly the result of increased stiffening of the natural crystalline lens.

Early non-surgical solutions to correct presbyopia include reading glasses or bifocal/progressive glasses and these presently remain the most commonly implemented remedial solutions for presbyopia. Contact lenses are now also being used to counter the effects of presbyopia through the use of "bifocal" (i.e., multifocal) contact lenses, or monovision where one eye is corrected for near vision and the other eye is corrected for distance vision. These are adequate solutions but do not correct the underlying problem and carry the inconvenience of dependence on glasses or contact lenses. While these solutions have disadvantages, they also have the advantages that they are not permanent and can be easily reversed and do not carry the attendant risks of surgical procedures.

Surgical options include such procedures as scleral relaxing incisions, laser thermokeratoplasty (LTK) and conductive keratoplasty (CK), corneal inlays, or accommodating/pseudo-accommodating intraocular lens implants. Scleral relaxing incisions have been found to be a poor solution at best. LTK/CK and corneal inlays treat the cornea and the effects of LTK/CK are generally not long-lasting, nor do these methods produce true accommodation, but are a version of either monovision or increased depth of field.

More recently, surgically implantable lenses have been developed to replace the eye's natural crystalline lens with an artificial lens in attempts to return accommodation back to the eye. The Crystalens®, an accommodating intraocular lens implant, is the first version of a monofocal lens designed to move in the eye in response to the natural movement of the ciliary body in accommodation. However, this lens does not provide sufficient dioptric range for good vision for near tasks. Pseudo-accommodating multi-focal intraocular lens implants (ReStor®, Array, ReZoom®, Tecnis MF®) provide adequate near vision but create optical distortions leading to less than ideal vision and do not provide the dynamic range of vision produced by natural accommodation.

Current intraocular surgical solutions for the treatment of presbyopia involve replacement of the malfunctioning crystalline lens. Multifocal lens implants are effective but compromise the quality of vision. Recipients of these lenses often experience visual artifacts including glare, loss of contrast sensitivity, and haloes. Further, these lenses are limited in the range of focus and do not provide a continuous dynamic range of focus from distance to intermediate to near distances. Currently, the only FDA approved accommodating intraocular lens (IOL) is the Crystalens® and has the advantage of being monofocal thereby providing a high quality image with minimal artifacts and distortion. However, the lens also has a downside wherein only a small range of accommodation is provided and the surgical results are variable, often requiring postoperative excimer laser surgery of the cornea for an ideal outcome. The lens only provides 1.5-2.0 diopters of accommodation whereas 2.5-3.5 diopters is needed for near vision tasks such as reading. An ideal IOL would have the advantages of a monofocal lens producing high image quality while minimizing glare and the other visual distortions of a multifocal lens. This ideal IOL would also provide a wide dynamic range of continuous accommodation of at least 4 diopters and couple seamlessly in real time to the natural neural and mechanical feedback mechanisms that are used to achieve accommodation in the human eye.

SUMMARY OF THE INVENTION

The present disclosure is generally directed to a presbyopia correcting intraocular lens implant that satisfies the need for a lens implant with a wide dynamic range of continuous accommodation. The presbyopia correcting intraocular lens implant for implanting in a human eye includes an implant body having a central lens enclosure and at least one stability tab extending therefrom. At least one ciliary body sensor senses movement of the eye's ciliary body. An electronic module is embedded in the implant body and includes a microprocessor communicative with the ciliary body sensor. A dynamic lens assembly is housed in the central lens enclosure and has a dynamic range of continuous accommodation. The lens implant also includes a renewable intraocular power supply.

In another aspect, the stability tab extends from a total periphery of the central lens enclosure.

In still another aspect, the implant includes a plurality of ciliary body sensors equally spaced about a periphery of the lens assembly.

In yet another aspect, the ciliary body sensors are combined ultrasonic emitters and sensors.

In a still further aspect, the ciliary body sensors are combined electromagnetic radiation emitters and sensors.

In another aspect, the dynamic lens assembly further includes an anterior lens defining a visual axis substantially perpendicular thereto and a posterior lens in axial registration with the anterior lens and translatable with respect thereto along the visual axis. An anterior electromotive ring on the anterior lens and a posterior electromotive ring on the posterior lens translate the posterior lens with respect to the anterior lens and are communicative with the microprocessor.

In another aspect, the anterior lens is a monofocal lens and the posterior lens is a plate of no lens power.

In a still further aspect, at least one of the lenses further comprises an electosensitive liquid crystal system that changes the refractive index of the lens in response to communication from the microprocessor/ciliary body sensor apparatus.

In yet another aspect, one of the anterior lens and the posterior lens is a plus diopter lens and the other of the lenses is a negative diopter lens or both are of plus power of equal or unequal magnitudes.

In another aspect, the coupler comprises a first electromagnetic ring at a periphery of the anterior lens and a second electromagnetic ring at a periphery of the posterior lens, and the coupler is responsive to the microprocessor communication to translate the posterior lens with respect to the anterior lens.

In still another aspect, the coupler comprises a plurality of accordion coupler elements interconnecting the anterior lens and the posterior lens at a periphery of the lens assembly, and the coupler is responsive to the microprocessor communication to translate the posterior lens with respect to the anterior lens.

In yet another aspect, the coupler comprises a plurality of interlocking coupler elements interconnecting the anterior and the posterior lenses at a periphery of the lens assembly, and further wherein the coupler is responsive to the microprocessor communication to translate the posterior lens with respect to the anterior lens.

In a further aspect the dynamic lens assembly includes an anterior flexible optical element and a posterior lens spaced from and in registration with the anterior flexible optical element. A sac surrounds the anterior flexible optical element and the posterior lens and a minimally compressible fluid fills the space between the anterior flexible optical element and the posterior lens. An anterior electromotive ring is positioned on the anterior lens and a posterior electromotive ring is positioned on the posterior lens for translating an outer periphery of the anterior flexible optic element with respect to the posterior lens and are communicative with the microprocessor.

In another aspect, the intraocular power supply comprises a rechargeable electrical storage device.

In still another aspect, the rechargeable electrical storage device consists of one of the group of a rechargeable battery and a capacitor bank.

In a further aspect, the intraocular power supply includes a photoelectric layer for converting light entering the eye to electrical power.

In yet another aspect, the intraocular power supply includes a Faraday inductive device driven by the natural saccadic and fixation movements of the eye.

In a still further aspect, the implant body is formed of a material that exhibits the characteristics of being biologically inert and electrically insulating.

In another aspect, a method of correcting presbyopia in the human eye includes surgically removing the natural crystalline lens in a user's eye and implanting a presbyopia correcting intraocular lens implant. The lens implant is of the type having a biologically inert body that includes at least one stability tab extending from a lens enclosure wherein the lens enclosure contains a lens assembly including an anterior lens and a posterior lens in registration and interconnected one to the other with a coupler and axially translatable one with respect to the other, each lens including on opposing faces an electromotive ring for providing attractive and repulsive force to achieve the axial translation and further wherein the posterior lens includes a plurality of ciliary body sensors about an outer periphery thereof, the implant further including an electrical power supply and a microprocessor in at least one electrical module embedded in the at least one stability tab. Electrical power is provided from the electrical power supply to the microprocessor to execute an instruction set and thereby causing the ciliary body sensors to emit an energy wave. The ciliary body sensors receive a reflection of the energy wave from the ciliary body of the eye. The elapsed time to receive the reflected energy wave is measured and the position of the ciliary body with respect to the implant is calculated as a function of the elapsed time to receive the reflected energy wave. The electromotive rings are energized as a function of the calculated ciliary body position thereby causing the anterior lens to translate with respect to the posterior lens a gap distance therebetween to provide a desired accommodation of the eye in response to the ciliary body position.

In another aspect, the energizing step includes energizing the electromotive rings with electromagnetic energy.

In a still further aspect, the energizing step includes energizing the electromotive rings with electrostatic energy.

In yet another aspect, the ciliary body sensors emit ultrasonic waves.

In another aspect, the ciliary body sensors emit light waves.

These and other features, aspects, and advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, where like numerals denote like elements and in which:

FIG. 7 presents a cross-sectional view of the presbyopia-correcting intraocular lens assembly shown in FIG. 5 and taken along the line 7-7, FIG. 5 wherein the lens elements achieve accommodation with attractive and repulsive forces and are in a first state of accommodation;

FIG. 8 presents a cross-sectional view of the presbyopia-correcting intraocular lens assembly shown in FIG. 5 and taken along the line 7-7, FIG. 5 wherein the lens elements are in a second state of accommodation;

FIG. 1 presents an elevation side view of a dual lens element embodiment incorporating an accordion coupling between a top and bottom lens;

Like reference numerals refer to like parts throughout the various views of the drawings.

DETAILED DESCRIPTION OF THE INVENTION

Figure 1:
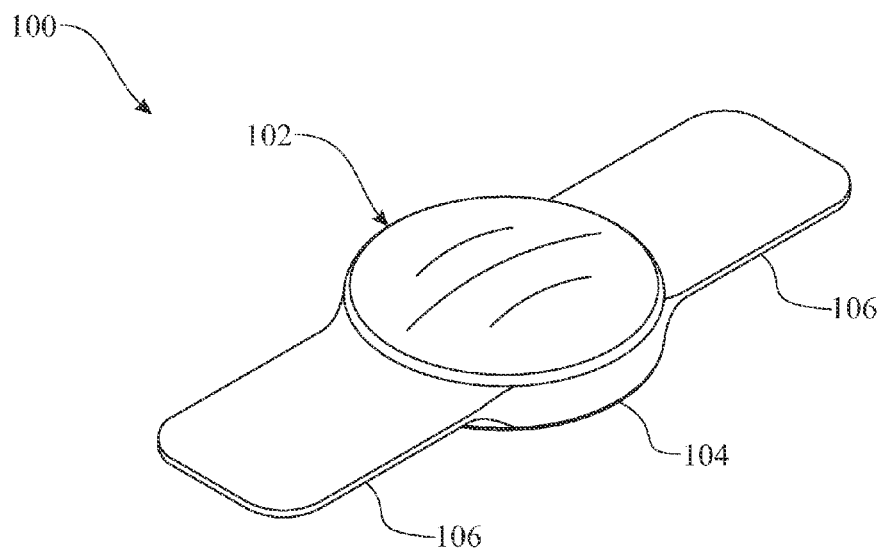
FIG. 1 presents a top isometric view of a presbyopia-correcting intraocular lens assembly embodying the present invention.
Figure 2:
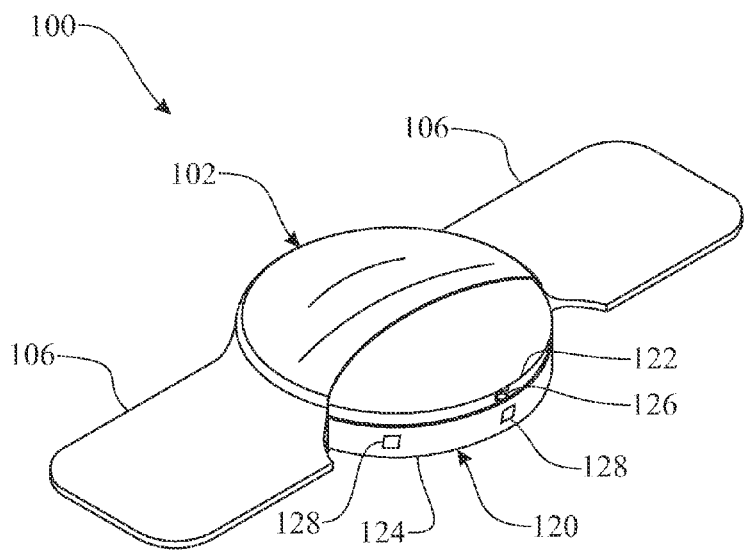
FIG. 2 presents a top isometric view of the presbyopia-correcting intraocular lens assembly of FIG. 1 with a portion of the lens assembly enclosure cut away.
Figure 3:
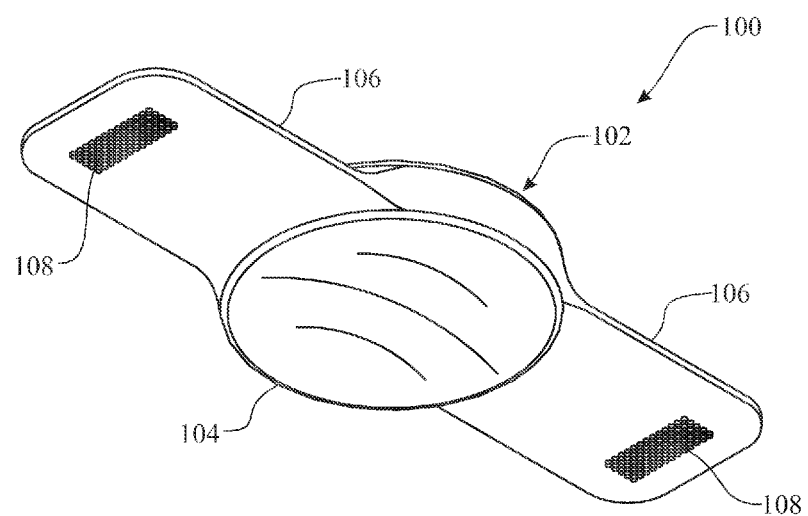
FIG. 3 presents a bottom isometric view of the presbyopia-correcting intraocular lens assembly of FIG. 1.
Figure 4:
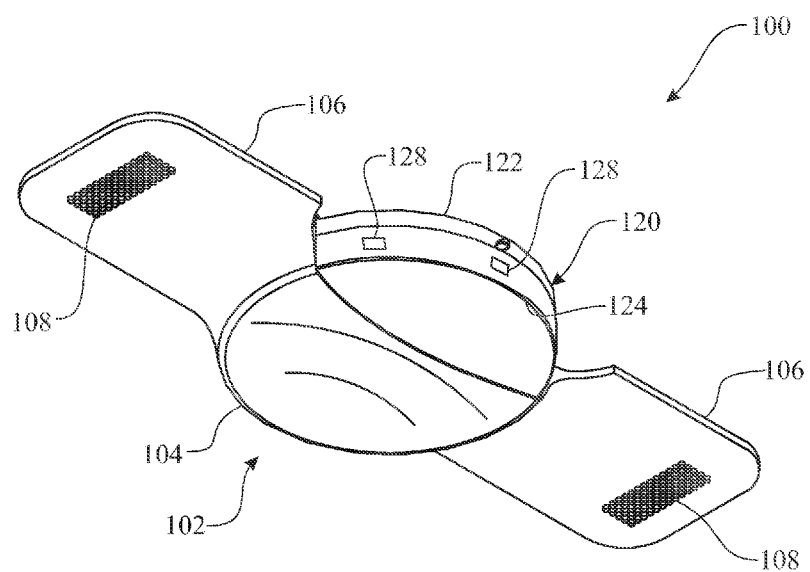
FIG. 4 presents a bottom isometric view of the presbyopia-correcting intraocular lens assembly of FIG. 1 with a portion of the lens assembly enclosure cut away.
Figure 5:
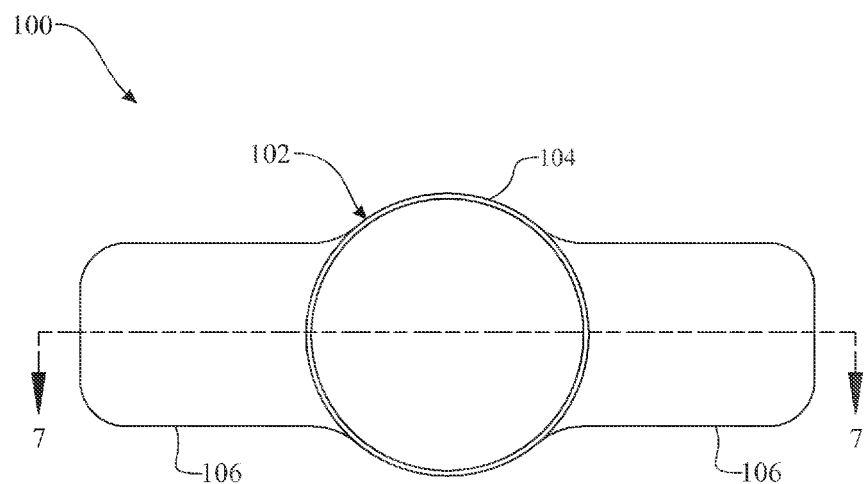
FIG. 5 presents a top plan view of the presbyopia-correcting intraocular lens assembly.
Figure 6:
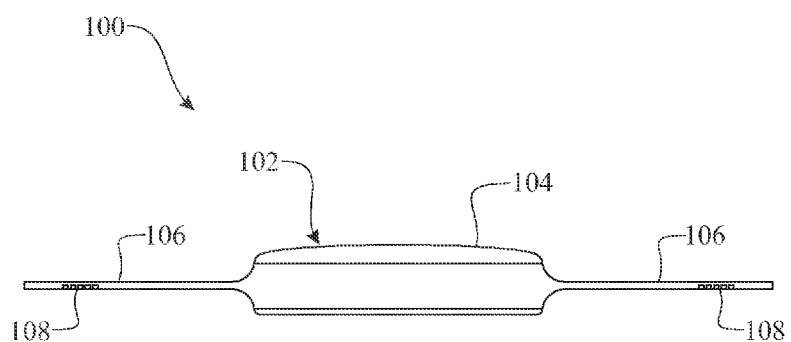
FIG. 6 presents an elevation side view of the presbyopia-correcting intraocular lens assembly.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Turning to the drawings, an intraocular lens implant 100 and its various components is illustrated in FIGS. 1-8 according to one of the preferred embodiments of the present invention. Intraocular lens implant 100 surgically replaces the natural crystalline lens in a human eye, and corrects the condition known as presbyopia. Intraocular lens implant 100 has a body 102 comprising a lens enclosure 104 having a lens assembly 120 enclosed therein and one or more stability tabs 106 extending from the lens enclosure 104. Since the body 102 is surgically implanted within the eye, the body 102 is typically fabricated from a material that is both biologically inert and electrically insulated. While the body 102 is illustrated as having two diametrically opposed stability tabs 106, the body 102 can have any number of haptics or stability tabs 106, including a single continuous peripheral stability tab extending about the entire periphery of the lens enclosure 104.

The lens assembly 120 enclosed within the lens enclosure 104 comprises an anterior lens 122 defining a visual axis "A" substantially perpendicular to the anterior lens 122 and a posterior lens 124 in registration with the anterior lens 122 along the visual axis "A". The anterior lens 122 and the posterior lens 124 are translatable one with respect to the other along the visual axis "A" to provide focusing over a range of at least 0 to 3 diopters and most preferably over a range of 0 to 4.5 diopters or greater. The anterior lens 122 and the posterior lens 124 include, on opposing facing surfaces and at peripheries thereof, an anterior electromotive ring 130 and a posterior electromotive ring 132, respectively. The electromotive rings 130, 132 are outside the visual axis of the lenses 122, 124 and the eye so as to be imperceptible to the individual in whose eye the implant is located. The electromotive rings 130, 132 provide attractive or repulsive forces one with respect to the other when energized so as to cause the anterior lens 122 and the posterior lens 124 to translate along the visual axis "A" one with respect to the other. As shown in FIGS. 7-8 electromotive rings 130, 132 operate to translate anterior lens 122 and posterior lens 124 one with respect to the other over a range represented by gap 134 to provide the desired accommodative focusing power for the eye in which intraocular implant 100 is implanted. It is anticipated that the default position (i.e., unpowered position when there is no energy in the electromotive rings) will set the lens assembly for distance vision both as a fail-safe should the power system fail and to conserve energy in the system in the resting state when the host subject is not accommodating.

The electromotive rings 130, 132 may operate either with electromagnetic force or with electrostatic force to induce the relative translation of the anterior lens 122 with respect to the posterior lens 124. An electrostatic force system is more advantageous since the anterior and posterior electromotive rings 130, 132 can be manufactured without using ferromagnetic material. MRI imaging is an ever increasingly used modality to diagnose human disease, and thus ferromagnetic elements within an intraocular lens implant may be a risk to a patient having an MRI imaging procedure. The strong magnetic forces used during an MRI imaging procedure may move the lens implant and damage delicate intraocular structures.

The lens assembly 120 can be either a monofocal lens arrangement or a two-lens arrangement. In the monofocal lens arrangement posterior lens 124 has no lens power and anterior lens 122 provides the necessary focal power for the eye as a result of its translated positioning along the visual axis "A". In another configuration, the anterior lens 122 and the posterior lens 124 can each be a monofocal lens, one of plus diopter power and one of minus diopter power or both of plus diopter power and translatable along the visual axis "A" one with respect to the other. The dual monofocal lens configuration of one plus diopter lens and one minus diopter lens or two plus diopter lenses achieves accommodation with smaller translational movements of the anterior lens 122 with respect to the posterior lens 124 than the configuration wherein only the anterior lens 122 provides the necessary focal power for accommodation.

The lens assembly further includes at least one and more preferably a plurality of ciliary body sensors 128 positioned at regularly spaced intervals about a periphery of the lens assembly 120 and more particularly about the outer periphery of posterior lens 124 or in the stability tabs 106. Ciliary body sensors 128 operate with ultrasonic wave technology, but may also operate with electromagnetic radiation such as a diode light transmitter or diode laser. Each ciliary body sensor 128 includes a transmitting and a receiving unit. Ciliary body sensors 128 emit short bursts of wave energy across the space between the periphery of the posterior lens 124 and ciliary body within the eye structure in which implant 100 is implanted. The waves are reflected back by the ciliary body and are detected by the receiver portion of the ciliary body sensor 128 without deforming the soft tissue of the ciliary body.

One or more electronic modules 108 are embedded within the stability tabs 106 and are electrically communicatively interconnected. One or more of the electronic modules 108 includes a microprocessor. The microprocessor executes an instruction set also stored within an electronic module 108.

Another of an electronic module 108 can include an electrical power supply such as a rechargeable battery or a capacitor bank for providing electrical power to operate the implant 100. The electronic module 108 can include a Faraday inductive device driven by the natural saccadic and fixation movements of the eye, including eye movements during REM sleep, which generates the power for storage in the capacitor bank or the rechargeable battery.

Another power generation feature can be a thin, biologically inert, optically transparent photoelectric film within the substance of the lens implant 100 such as a semiconductor film or carbon nanotube assembly. Alternatively, the power generation feature can be a continuous or segmental ring or scatter elements of an opaque photoelectric material within the lens assembly 120 optic, since a recognized optical principle is that portions of a lens may be blocked which, although diminishing the intensity of the light available to form an image, still allows for the formation of a clear image.

Another possible power generation feature is a long-acting rechargeable battery that can be recharged through a noncontact external device which, when placed over the skin or surface of the eye can be used to recharge the endogenous battery of the lens implant. One possible such configuration is two rotating magnet gyros wherein an external gyro is driven by a battery or household power. The spinning external gyro causes an internal magnet to spin and thereby generate electric current to charge the internal battery.

Within the intraocular implant 100, the microprocessor(s) in electronic module(s) 108 is electrically interconnected with the internal battery in the same or in a separate electronic module 108, and communicatively interconnected with the ciliary body sensors 128 and the electromotive rings 130,132 for controlled operation of the lens implant 100 to provide the user with a practical accommodative range (3-4 diopter or more) of corrected presbyopia function.

Figure 9:
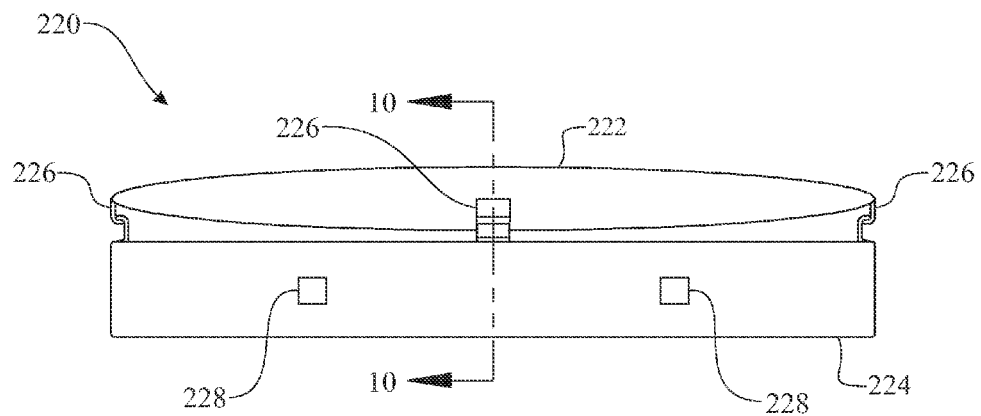
FIG. 9 presents an elevation side view of a dual lens element embodiment incorporating a clip coupling between a top and bottom lens.
Figure 10:
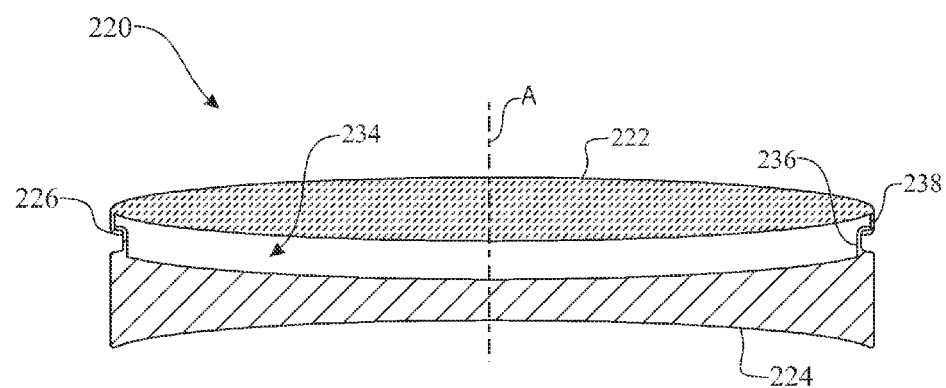
FIG. 10 presents a cross-sectional view of the presbyopia-correcting intraocular lens assembly shown in FIG. 9 and taken along the line 10-10, FIG. 9.

As illustrated in FIGS. 9-10 a lens assembly 220 can include an anterior lens 222 and a posterior lens 224 translatable one with respect to the other over a range represented by gap 234. Posterior lens 224 includes a plurality of ciliary body sensors 228 about an outer periphery thereof. A plurality of interlocking couplers 226 are located about a periphery of lens assembly 220. Each interlocking coupler 226 includes an anterior interlocking member 238 affixed to anterior lens 222 and an opposing posterior interlocking member 236 affixed to posterior lens 224. The opposed interlocking members 236, 238 permit free translation along visual axis "A" of anterior lens 222 with respect to posterior lens 224 to the maximum gap 234 permitted until the interengagement of anterior interlocking member 238 with posterior interlocking member 236.

Figure 11:
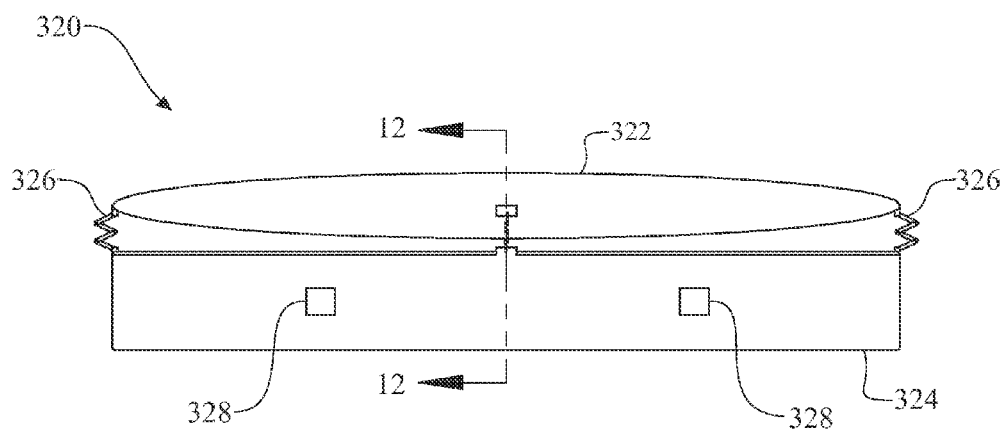
Figure 12:
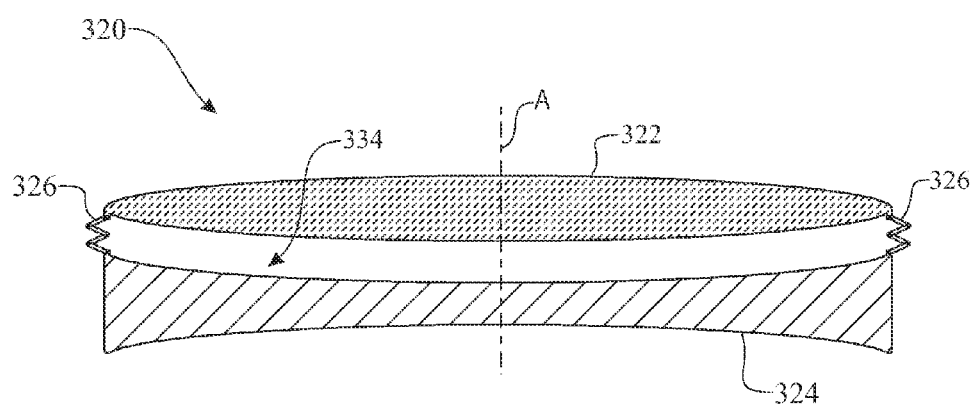
FIG. 12 presents a cross-sectional view of the presbyopia-correcting intraocular lens assembly shown in FIG. 11 and taken along the line 12-12, FIG. 11.

In a further embodiment as illustrated in FIGS. 11-12, a lens assembly 320 can include an anterior lens 222 and a posterior lens 224 translatable one with respect to the other over a range represented by gap 334. Posterior lens 324 includes a plurality of ciliary body sensors 328 about an outer periphery thereof. A plurality of accordion couplers 326 are located about a periphery of lens assembly 320. Each accordion coupler 326 has one end thereof affixed to the anterior lens 322 and an opposite end affixed to posterior lens 324. The accordion couplers 326 permit free translation along visual axis "A" of anterior lens 322 with respect to posterior lens 324 to the maximum gap 334 permitted until the full extension of accordion coupler 326 is reached to achieve the maximum gap 334.

Figure 13:
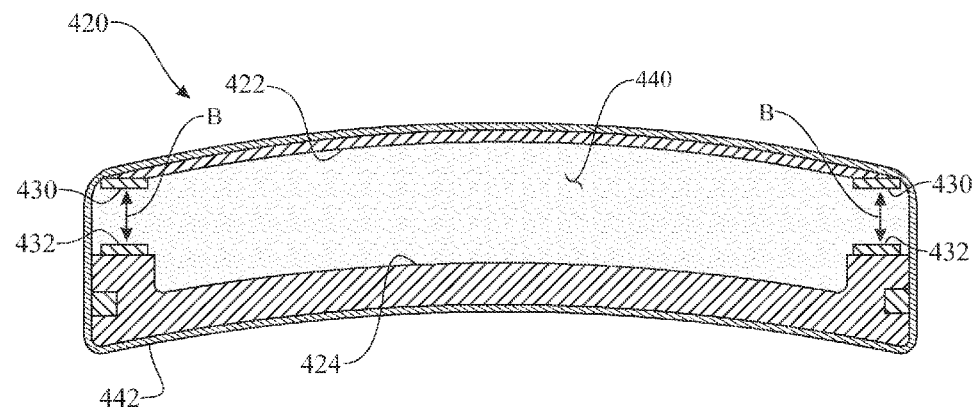
FIG. 13 presents a cross-sectional view of the presbyopia-correcting intraocular lens assembly, wherein the anterior lens is flexible.
Figure 14:
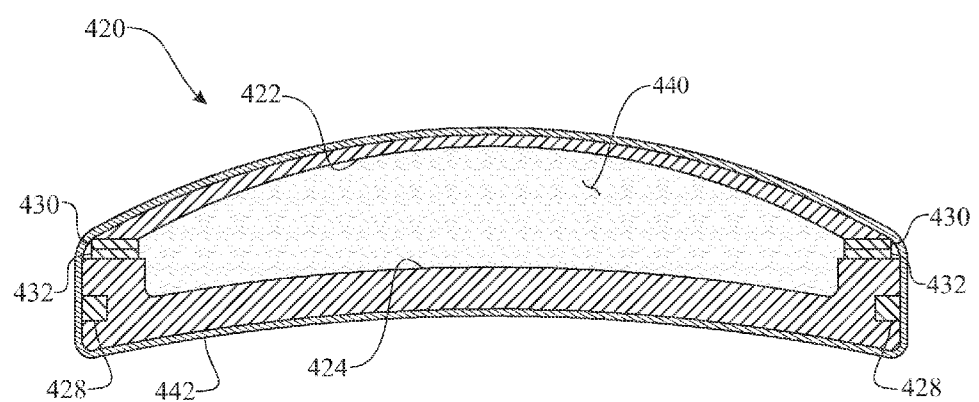
FIG. 14 presents the cross-sectional view of the presbyopia-correcting intraocular lens assembly of FIG. 13, wherein the anterior lens has flex.

A fluid filled lens assembly 420 is shown as a further embodiment in FIGS. 13-14. Lens assembly 420 includes a sac 442 containing a posterior lens 424 and an anterior flexible optic element 422 spaced from the posterior lens 424. The space between posterior lens 424 and anterior flexible optic element 422 is filled with a minimally compressible fluid 440. Those practiced in the art will readily recognize that anterior element 422 and posterior element 424 can each be some combination of plus (convex), planar, or minus (concave) lenses. Both elements 422, 424 may be flexible or one of elements 422, 424 may be rigid and one flexible within the anticipated scope of the embodiment depending on the required optics needed for a particular patient. Silicone or other like material or a combination of a flexible material for the anterior flexible optic element 422 and a stiffer material for the sac 422 can be used.

The anterior flexible optic element 422 includes an electromotive ring 430 affixed to a posterior surface of element 422 at an outer periphery thereof. In similar manner, posterior lens 424 includes an electromotive ring 432 affixed to an anterior surface of lens 424 at an outer periphery thereof and substantially in opposition to electromotive ring 430. Electromotive rings 430, 432 provide attractive or repulsive forces one with respect to the other when energized so as to cause the outer portions of elements 422, 424 to translate according to arrows "B" (FIG. 13). Ciliary body sensors 428 are positioned about an outer periphery of posterior lens 424 to measure the position of the ciliary body as previously described above.

In operation, the electromotive rings 430, 432 provide attractive or repulsive forces one with respect to the other when energized so as to cause the outer edge of the anterior flexible optic element 422 and the electromotive ring 430 to translate toward the electromotive ring 432 according to arrows "B" (FIG. 13). Since the fluid 440 is minimally compressive, the anterior flexible optic element 422 adopts a steeper curve (FIG. 14) thereby altering the accommodative optical power of lens assembly 420. Both the anterior and the posterior surfaces may be flexible and change shape with movement of the electromotive rings 430, 432, or one may be substantially rigid and static and the other may translate and change curvature with respect to it. Accommodation may be achieved simply with a change in the curvature or there may be a combination of change in curvature combined with axial translation to achieve accommodation.

In using the disclosed embodiment for correction of the condition of presbyopia in an eye of a human, the natural crystalline lens is surgically removed and is replaced by a presbyopia correcting intraocular lens implant 100. An electrical power supply as a part of an electronic module 108 embedded in a stability tab 106 of the lens implant 100 provides electrical power to a microprocessor in the same or another electronic module 108 in the same or another stability tab 106. The microprocessor in execution of an instruction set retained in an electronic memory also embedded in electronic module 108 causes ciliary body sensors 128 to emit wave energy in real time at regular intervals such as at a rate of ten times per second. Each ciliary body sensor also receives the portion of the energy wave reflected from the ciliary body within the eye structure. The position of the ciliary body is then calculated by the microprocessor based upon the elapsed time the energy wave was transmitted and the reflected energy wave was received. The position of the ciliary body and the motion of the ciliary body thereof over a plurality of samplings of the ciliary body sensors 128 are calculated by the microprocessor to determine the amount of focusing required by the lens assembly 120 within lens enclosure 104 of implant 100. The microprocessor in electronic module 108 then energizes the electromotive rings 130, 132 with electrical power in an amount to induce the axial translation of anterior lens 122 with respect to posterior lens 124. This axial translation thereby adjusts the gap 134 between the anterior lens 122 and the posterior lens 124 of lens assembly 120 to provide the desired focus adjustment to the user's eye to achieve the needed accommodation for the user to focus on near objects such as the page of a book for reading. This process is continually repeated at the predetermined rate (i.e. ten times per second) to approach a 'real time' response rate for accommodation as the user would normally experience with a natural crystalline lens. This dynamic self-contained mechanism is coupled to the natural accommodative neural feedback loop without the need for direct contact with the soft tissues of the ciliary body. The ciliary body soft tissue is not teleologically designed for mechanical constriction of the natural crystalline lens or an artificial lens implant and would likely fatigue or fail over time with repeated contact with the artificial lens implant, a characteristic of contemporary artificial accommodating lens implant designs.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A presbyopia correcting intraocular lens implant for implanting in a human eye, said intraocular lens implant comprising:
    an implant body having a central lens enclosure and at least one stability feature extending therefrom;
    at least one ciliary body sensor for sensing movement of the eye's ciliary body;
    an electronic module embedded in said implant body, said module including a microprocessor communicative with said at least one ciliary body sensor;
    a dynamic lens assembly housed in said central lens enclosure and having a dynamic range of continuous accommodation, said dynamic lens assembly further comprising:
        an anterior lens defining a visual axis substantially perpendicular thereto;
        a posterior lens in registration with said anterior lens and translatable with respect thereto along said visual axis;
        an anterior electromotive ring integrated with said anterior lens and an opposing posterior electromotive ring integrated with said posterior lens for translating said posterior lens with respect to said anterior lens and communicative with said microprocessor; and
        a dynamic lens assembly coupling system limiting the range of translation of said anterior and posterior lenses with respect to one another; and,
    a renewable intraocular power supply.

2. An intraocular lens implant according to claim 1 wherein said at least one stability feature extends from a total periphery of said central lens enclosure.

3. An intraocular lens implant according to claim 1 wherein said at least one ciliary body sensor is integrated into said dynamic lens assembly.

4. An intraocular lens implant according to claim 3 wherein said ciliary body sensors are combined ultrasonic emitters and sensors.

5. An intraocular lens implant according to claim 3 wherein said ciliary body sensors are combined electromagnetic radiation emitters and sensors.

6. An intraocular lens implant according claim 1 wherein at least one of said lenses further comprises an electrosensitive liquid crystal system that changes the refractive index of said at least one lens in response to said microprocessor communication.

7. An intraocular lens implant according to claim 1 wherein one of said anterior lens and said posterior lens is a plus diopter lens and the other of said lenses is a negative diopter lens.

8. An intraocular lens implant according to claim 1 wherein said anterior and posterior electromagnetic rings are responsive to said microprocessor communication to translate said posterior lens with respect to said anterior lens within the translation range limitation of said dynamic lens assembly coupling system.

9. An intraocular lens implant according to claim 1 wherein said dynamic lens assembly coupling system further comprises at least one accordion coupler element interconnecting said anterior lens and said posterior lens at a periphery of said lens assembly.

10. An intraocular lens implant according to claim 1 wherein said coupling system further comprises at least one pair of interlocking coupler elements interconnecting said anterior and said posterior lenses at a periphery of said lens assembly.

11. An intraocular lens implant according to claim 1 wherein a first one of said anterior and posterior lenses comprises a flexible optical element a second one of said anterior and posterior lenses comprises an opposing power optical element, said opposing power optical element selected from the group consisting of a fixed power optical element and a flexible power optical element, said first and second lenses spaced apart from and in registration with one another, and wherein said dynamic lens assembly further comprises:
    a sealed flexible enclosure surrounding said flexible optical element and said opposing power optical element; and a compressible fluid filling said space between said flexible optical element and said power optical element;

wherein said electromotive rings cooperate to translate an outer periphery of said flexible optical element to induce a change in curvature thereof.

12. An intraocular lens implant according to claim 1 wherein said intraocular renewable intraocular power supply further comprises a rechargeable electrical storage device.

13. An intraocular lens implant according to claim 12 wherein said intraocular renewable power supply includes a photoelectric layer for converting light entering the eye to electrical power.

14. An intraocular lens implant according to claim 12 wherein said rechargeable electrical storage device includes a Faraday inductive device driven by the natural saccadic and fixation movements of the eye.

15. An intraocular lens implant according to claim 1 wherein said implant body is formed of a material that exhibits the characteristics of being biologically inert and electrically insulating.

16. A method of correcting presbyopia in the human eye comprising the steps of:

providing a presbyopia correcting intraocular lens implant for implanting in a human eye, the intraocular lens implant including:

an implant body having a central lens enclosure and at least one stability feature extending therefrom;

at least one ciliary body sensor for sensing movement of the eye's ciliary body;

an electronic module embedded in said implant body, said module including a microprocessor communicative with said at least one ciliary body sensor;

a dynamic lens assembly housed in said central lens enclosure and having a dynamic range of continuous accommodation, said dynamic lens assembly including:

an anterior lens defining a visual axis substantially perpendicular thereto;

a posterior lens in registration with said anterior lens and translatable with respect thereto along said visual axis;

an anterior electromotive ring integrated with said anterior lens and an opposing posterior electromotive ring integrated with said posterior lens for translating said posterior lens with respect to said anterior lens and communicative with said microprocessor; and a dynamic lens assembly coupling system limiting the range of translation of said anterior and posterior lenses with respect to one another, and, a renewable intraocular power supply;

removing surgically the natural crystalline lens from said human eye;

implanting said presbyopia correcting intraocular lens implant within said eye in place of said removed natural crystalline lens providing electrical power from the electrical power supply to the microprocessor to execute an instruction set;

causing said at least one ciliary body sensor to emit an energy wave;

receiving a reflection of the energy wave from the ciliary body of the eye;

measuring the elapsed time to receive the reflected energy wave;

calculating as a function of the elapsed time to receive the reflected energy wave, the position of the ciliary body with respect to the implant;

energizing the electromotive rings as a function of the calculated ciliary body position; and causing the anterior lens to translate with respect to the posterior lens a gap distance therebetween to provide a desired accommodation of the eye.

17. The method of correcting presbyopia according to claim 16 wherein the energizing step includes energizing the electromotive rings with electromagnetic energy.

18. The method of correcting presbyopia according to claim 16 wherein the ciliary body sensors emit one electromagnetic wave selected from the group consisting of light waves and ultrasonic waves.

* * * * *